US010226500B2

(12) United States Patent
Li et al.

(10) Patent No.: US 10,226,500 B2
(45) Date of Patent: Mar. 12, 2019

(54) USE OF THE CHINESE MEDICINE COMPOSITION AND DIANXIANNING IN THE PREPARATION OF A MEDICAMENT FOR PREVENTING OR TREATING ALZHEIMER'S DISEASES

(71) Applicant: Lanzhou University, Lanzhou, Gansu (CN)

(72) Inventors: Hongyu Li, Gansu (CN); Dong Wang, Gansu (CN); Dejuan Zhi, Gansu (CN); Yang Li, Gansu (CN); Yinghui Li, Gansu (CN); Xiaoyu Chen, Gansu (CN)

(73) Assignee: Lanzhou University, Lanzhou, Gansu (CN)

( * ) Notice: Subject to any disclaimer, the term of this patent is extended or adjusted under 35 U.S.C. 154(b) by 130 days.

(21) Appl. No.: 15/390,386

(22) Filed: Dec. 23, 2016

(65) Prior Publication Data

US 2017/0157192 A1    Jun. 8, 2017

Related U.S. Application Data

(63) Continuation-in-part of application No. PCT/CN2014/080789, filed on Jun. 26, 2014.

(51) Int. Cl.

| | |
|---|---|
| *A61K 36/00* | (2006.01) |
| *A61K 36/882* | (2006.01) |
| *A61K 36/888* | (2006.01) |
| *A61K 9/10* | (2006.01) |
| *A61K 9/14* | (2006.01) |
| *A61K 9/20* | (2006.01) |
| *A61K 9/48* | (2006.01) |
| *A61K 36/185* | (2006.01) |
| *A61K 36/39* | (2006.01) |
| *A61K 36/47* | (2006.01) |
| *A61K 36/534* | (2006.01) |
| *A61K 36/74* | (2006.01) |
| *A61K 31/045* | (2006.01) |
| *A61K 36/35* | (2006.01) |

(52) U.S. Cl.
CPC .............. *A61K 36/882* (2013.01); *A61K 9/10* (2013.01); *A61K 9/14* (2013.01); *A61K 9/20* (2013.01); *A61K 9/48* (2013.01); *A61K 31/045* (2013.01); *A61K 36/185* (2013.01); *A61K 36/35* (2013.01); *A61K 36/39* (2013.01); *A61K 36/47* (2013.01); *A61K 36/534* (2013.01); *A61K 36/74* (2013.01); *A61K 36/888* (2013.01)

(58) Field of Classification Search
CPC ....................................................... A61K 36/00
See application file for complete search history.

(56) References Cited

FOREIGN PATENT DOCUMENTS

| CN | 1084756 A | 4/1994 |
|---|---|---|
| CN | 1134298 A | 10/1996 |
| CN | 101732515 A | 6/2010 |

OTHER PUBLICATIONS

English translation of International Search Report and Written Opinion for PCT/CN2014/080789, dated Mar. 13, 2015, 6 pages.
He, Y. et al. "Effects of rhynchophylline on GluN1 and GluN2B expressions in primary cultured hippocampal neurons." *Fitoterapia* 98: 166-173, published online Aug. 7, 2014.
Kwan P. and Brodie M.J. "Neuropsychological effects of epilepsy and antiepileptic drugs." *The Lancet* 357, No. 9251: 216-222, Jan. 20, 2001.
Li et al., "Clinical Analysis on Dianxianning Tablet for Refractory Epilepsy," *Journal of Medical Forum* 25, No. 14 (2004): 70 (no translation).
News of UCSF (News Center of University of California San Francisco). "Epilepsy Drug Could Help with Alzheimer's-Related Memory Loss." Published Aug. 6, 2012; accessed Mar. 23, 2017. Retrieved from https://www.ucsf.edu/news/2012/08/12481/epilepsy-drug-could-help-alzheimers-related-memory-loss, 3 pages.
Palop, J. and Mucke, L. "Synaptic depression and aberrant excitatory network activity in Alzheimer's disease: two faces of the same coin?" *Neuromolecular Medicine* 12, No. 1: 48-55, published online Oct. 17, 2009.
Qing, H. et al. "Valproic acid inhibits Aβ production, neuritic plaque formation, and behavioral deficits in Alzheimer's disease mouse models." *Journal of Experimental Medicine* 205, No. 12 (2008): 2781-2789.
Sanchez, P. et al. "Levetiracetam suppresses neuronal network dysfunction and reverses synaptic and reverses synaptic and cognitive deficits in an Alzheimer's disease model." *Proceedings of the National Academy of Sciences* 109, No. 42: E2895-E2903, published online Aug. 6, 2012.
Tian., S. et al. "Effects of different fractions of *Acori graminei* rhizoma extracts on learning and memory abilities in Aβ-induced Alzheimer disease mice." *Chin. J. Pathophysiol* 28 (2012): 159-162, with English-language abstract.
Ya-ming L. "Thoughts and methods of traditional Chinese medicament in preventing and treating Alzheimer disease." *Chinese Journal of Clinical Rehabilitation* 9, No. 24, (2005): 144-146, with English-language abstract.
Zhang, M.Y. et al. "Lamotrigine attenuates deficits in synaptic plasticity and accumulation of amyloid plaques in APP/PSI transgenic mice." *Neurobiology of Aging* 35, No. 12: 2713-2725, published online Jun. 16, 2014.

(Continued)

*Primary Examiner* — Qiuwen Mi
(74) *Attorney, Agent, or Firm* — Klarquist Sparkman, LLP

(57) ABSTRACT

Disclosed is a use of the Chinese medicine composition and Dianxianning in the preparation of a medicament for preventing or treating Alzheimer's disease. As indicated by the experiments, the Chinese medicine composition and Dianxianning have a significant inhibiting effect on palsy phenotype in pathological models of animals with Alzheimer's disease, and this indicates that the Chinese medicine composition and Dianxianning can be used to prevent or treat Alzheimer's disease.

7 Claims, 5 Drawing Sheets

(56) References Cited

OTHER PUBLICATIONS

First Search for Priority Application CN20151354410 (Sep. 25, 2017). 1 p.
Notification to Grant Patent Right for Invention of Priority CN20151354410 (Dec. 14, 2017). 3 pp.
Zhen, J., et al., "The Clinical Randomized Double-blinded Study on Therapeutic Effect of Diancianning Pian to Patients with Epilepsy," *Inner Mongolia Med. J.* 2010, pp. 904-908 (with English-language abstract).

USE OF THE CHINESE MEDICINE COMPOSITION AND DIANXIANNING IN THE PREPARATION OF A MEDICAMENT FOR PREVENTING OR TREATING ALZHEIMER'S DISEASES

CROSS REFERENCE TO RELATED APPLICATION

This is a continuation-in-part of International Application No. PCT/CN2014/080789, filed Jun. 26, 2014, which application is incorporated herein by reference in its entirety.

FIELD

The present invention relates to the novel application of the Chinese medicine composition and Dianxian Ning (DXN), and in particular to the use of the Chinese medicine composition and DXN in the preparation of a medicament for preventing or treating Alzheimer's disease (AD). It belongs to the field of traditional Chinese medicament.

BACKGROUND

Alzheimer's disease (AD) is a kind of neurodegenerative diseases, and progressive cognitive impairment and memory impairment are the principal characters of AD. Clinically, memory impairment, aphasia, apraxia, agnosia, visuospatial skill impairment, executive dysfunction as well as personality and behavioral changes are the judgment criteria of AD. Currently, there are two kinds of medicaments used to treat AD, acetylcholinesterase inhibitors (such as galantamine) and N-methyl-D-aspartate receptor (NMDA receptor) antagonist (such as memantine), but these drugs are expensive and the side-effects were serious (such as hallucinations, chaotic consciousness, dizziness, headaches and tiredness and the like). Above all these medicaments can only control the patient's condition but cannot reverse it.

Pathogenesis of AD have been investigated for many years by modern medicament, but because of its complex etiology, the pathogenesis of AD is still not clear up to now. β-amyloid protein (Aβ) theory is the mainstream theory of AD, which states that abnormal deposition of Aβ in the brain of patients directly or indirectly affects neurons and glial cells by a series of cascade reactions such as radical reaction, mitochondrial oxidative damage and inflammation, eventually leading to neuronal dysfunction or death, thereby causing memory loss and cognitive impairment, and ultimately resulting in dementia.

Aβ aggregates in the cerebral cortex and hippocampus and subsequently forms senile plaques (SP), which is one of the most major pathological features of AD. Aβ is an important substance leading to AD, which can effectively weaken the structure and function of synap. Therefore, Aβ has become a recognized drug targets in screening medicaments for the prevention or treatment of AD.

Etiology and pathogenesis of AD is complicated, the current medicaments on the market will lead to drug resistance and serious adverse reactions. Traditional Chinese medicaments apply an active multi-component and multi-target approach in the treatment of a serious of diseases, so that Chinese medicaments have obvious advantages on AD treatment.

There may exist close relationship between epilepsy and AD, and Aβ has been identified as the link between these two disorders. In fact, antiepileptic drugs have been involved in preclinical or clinical trial for treating AD. Levetiracetam can suppress neuronal network dysfunction and reverse AD damage and cognitive impairment in mice. Lamotrigine can attenuate deficits in synaptic plasticity and accumulation of amyloid plaques in APP/PS1 transgenic mice and effectively promote their learning memory behavior. Valproic acid can inhibit Aβ generation, neuritic plaque production, ameliorate cognitive performance in AD mice, but it is unlikely to affect patient cognitive function. Carbamazepine and phenytoin can even impair patient cognitive function. Anyhow, repurposing antiepileptic drugs is still available to discover potential anti-AD drug candidates.

News Center of University of California San Francisco reported that antiepileptic drugs named levetiracetam can effectively improve the memory loss caused by Alzheimer, and can reduce damages of the animal model for Alzheimer on Jun. 8, 2012.

The active ingredients of *Valeriana* Jatamansi Jones, Acorus tatarinowii, and Ramulus Uncariae cum Uncis all have potential effect on Alzheimer's treatment.

So far, there are only five FDA-approved anti-AD drugs on the market. Unfortunately, they can only delay the onset of dementia, and none of them can halt or reverse the disease. These medicaments for treating AD have never met the medical need, and it is urgent to find effective and safe drugs against AD.

SUMMARY

An object of the present invention is to provide novel application of the Chinese medicine composition, and in particular the use of the Chinese medicine composition for preventing or treating AD.

The Chinese medicine composition in the present invention comprises *Valeriana* Jatamansi, Rhizoma Acori Tatarinowii (Acorns tatarinowii Schott), Ramulus Uncariae cum Uncis, Semen Pharbitidis, Semen Euphorbiae, Radix et Rhizoma *Valerianae*, Rhizoma et Radix Nardostachys (Nardostachyos Root and Rhizome), and menthol crystal, among others.

The Chinese medicine composition in the present invention comprises the following components in part by weight: 300 to 600 parts of *Valeriana* Jatamansi, 300 to 600 parts of Rhizoma Acori Tatarinowii, 150 to 300 parts of Ramulus Uncariae cum Uncis, 150 to 300 parts of Semen Pharbitidis, 150 to 300 parts of Rhizoma et Radix Nardostachys 10 to 35 parts of Semen Euphorbiae, 0.45 to 0.75 parts of *Valeriana* officinalis and 0.1 to 0.6 parts of menthol crystal.

Preferably, the Chinese medicine composition in the present invention comprises the following components in part by weight: 300 to 500 parts of *Valeriana* Jatamansi, 300 to 500 parts of Rhizoma Acori Tatarinowii, 150 to 200 parts of Ramulus Uncariae cum Uncis, 150 to 200 parts of Semen Pharbitidis, 150 to 200 parts of Rhizoma et Radix Nardostachys 10 to 15 parts of Semen Euphorbiae, 0.45 to 0.62 parts of *Valeriana officinalis* and 0.1 to 0.3 parts of menthol crystal.

Preferably, the Chinese medicine composition in the present invention comprises the following components in part by weight: 500 to 600 parts of *Valeriana* Jatamansi, 500 to 600 parts of Rhizoma Acori Tatarinowii, 200 to 300 parts of Ramulus Uncariae cum Uncis, 200 to 300 parts of Semen Pharbitidis, 200 to 300 parts of Rhizoma et Radix Nardostachys 15 to 35 parts of Semen Euphorbiae, 0.62 to 0.75 parts of *Valeriana* officinalis and 0.3 to 0.6 parts of menthol crystal.

Another object of the present invention is to provide novel application of the Chinese medicine composition, and in particular the use of the Chinese medicine composition in the preparation of a medicament for preventing or treating AD.

The Chinese medicine composition in the present invention comprises *Valeriana* Jatamansi, Rhizoma Acori Tatarinowii (Acorns tatarinowii Schott), Ramulus Uncariae cum Uncis, Semen Pharbitidis, Semen Euphorbiae, Radix et Rhizoma *Valerianae*, Rhizoma et Radix Nardostachys (Nardostachyos Root and Rhizome), and menthol crystal, among others.

The Chinese medicine composition in the present invention comprises the following components in part by weight: 300 to 600 parts of *Valeriana* Jatamansi, 300 to 600 parts of Rhizoma Acori Tatarinowii, 150 to 300 parts of Ramulus Uncariae cum Uncis, 150 to 300 parts of Semen Pharbitidis, 150 to 300 parts of Rhizoma et Radix Nardostachys 10 to 35 parts of Semen Euphorbiae, 0.45 to 0.75 parts of *Valeriana* officinalis and 0.1 to 0.6 parts of menthol crystal.

Preferably, the Chinese medicine composition in the present invention comprises the following components in part by weight: 300 to 500 parts of *Valeriana* Jatamansi, 300 to 500 parts of Rhizoma Acori Tatarinowii, 150 to 200 parts of Ramulus Uncariae cum Uncis, 150 to 200 parts of Semen Pharbitidis, 150 to 200 parts of Rhizoma et Radix Nardostachys 10 to 15 parts of Semen Euphorbiae, 0.45 to 0.62 parts of *Valeriana* officinalis and 0.1 to 0.3 parts of menthol crystal.

Preferably, the Chinese medicine composition in the present invention comprises the following components in part by weight: 500 to 600 parts of *Valeriana* Jatamansi, 500 to 600 parts of Rhizoma Acori Tatarinowii, 200 to 300 parts of Ramulus Uncariae cum Uncis, 200 to 300 parts of Semen Pharbitidis, 200 to 300 parts of Rhizoma et Radix Nardostachys 15 to 35 parts of Semen Euphorbiae, 0.62 to 0.75 parts of *Valeriana* officinalis and 0.3 to 0.6 parts of menthol crystal.

Another object of the present invention is to provide novel application of Dianxian Ning (DXN), and in particular the use of DXN in the preparation of a medicament for preventing or treating AD. Dianxianning in the present invention comprises the following components in part by weight: 500 parts of *Valeriana* Jatamansi, 500 parts of Rhizoma Acori Tatarinowii, 200 parts of Ramulus Uncariae cum Uncis, 200 parts of Semen Pharbitidis, 200 parts of Rhizoma et Radix Nardostachys, 15 parts of Semen Euphorbiae, 0.62 parts of *Valeriana* officinalis and 0.3 parts of menthol crystal.

The forms of the DXN can be tablets, pills, capsules, oral solution or granules. Different forms of DXN cannot affect the action of it on preventing or treating AD. DXN used in the present invention is DXN tablet.

DXN is consist of eight Chinese medicament herbs, namely *Valeriana* Jatamansi, Rhizoma Acori Tatarinowii (Acorns tatarinowii Schott), Ramulus Uncariae cum Uncis, Semen Pharbitidis, Semen Euphorbiae, Radix et Rhizoma *Valerianae*, Rhizoma et Radix Nardostachys (Nardostachyos Root and Rhizome), and menthol crystal, among others. Currently, DXN is used for treating the wind-phlegm invading upward induced epilepsy, or hysteria, insomnia.

The present invention employed the transgenic *C. elegans* strain CL4176 as a pathological model to evaluate the effect of the Chinese medicine and DXN on preventing or treating AD. The principle of Aβ theory of AD is based on that Aβ aggregates in the cerebral cortex and hippocampus and subsequently forms senile plaques (SP), which is one of the most major pathological features of AD. Toxic Aβ can effectively weaken the structure and function of synapses, and cause memory impairment on the AD patients. Transgenic *C. elegans* strain CL4176 which expresses the human Aβ species in the muscle tissue that can induce Aβ-dependent paralysis at 25° C. was used in the present invention. Aβ aggregates in the muscle tissue, eventually resulting in the paralysis of CL4176. The medicament acts on *C. elegans* strain CL4176. If a drug can significantly delay the progress of the paralysis, the drug is likely to be effective in the prevention or treatment of AD.

*C. elegans* are sensitive to environmental changes, and drug toxicity can be accurately evaluated by using *C. elegans*. The body length is one of the most commonly used indictors of developmental toxicity. If the body length of worms is significantly reduced after treated with a drug, then the drug may have serious developmental toxicity on *C. elegans*.

Compared with the prior art, the present invention has the following beneficial effects:

The present invention evaluated the protect effect of the Chinese medicine and DXN on the toxicity Aβ-dependent paralysis of transgenic *C. elegans* strain CL4176, the results showed that the Chinese medicine and DXN can significantly delay the progress of the paralysis, indicated that the Chinese medicine and DXN have the potential to prevent or treat AD.

The present invention discloses that the Chinese medicine and DXN may be a useful drug in preventing or treating AD.

BRIEF DESCRIPTION OF THE DRAWINGS

Embodiments of the present invention will be described in further detail with reference to the accompanying drawings.

DETAILED DESCRIPTION

Figure 1:
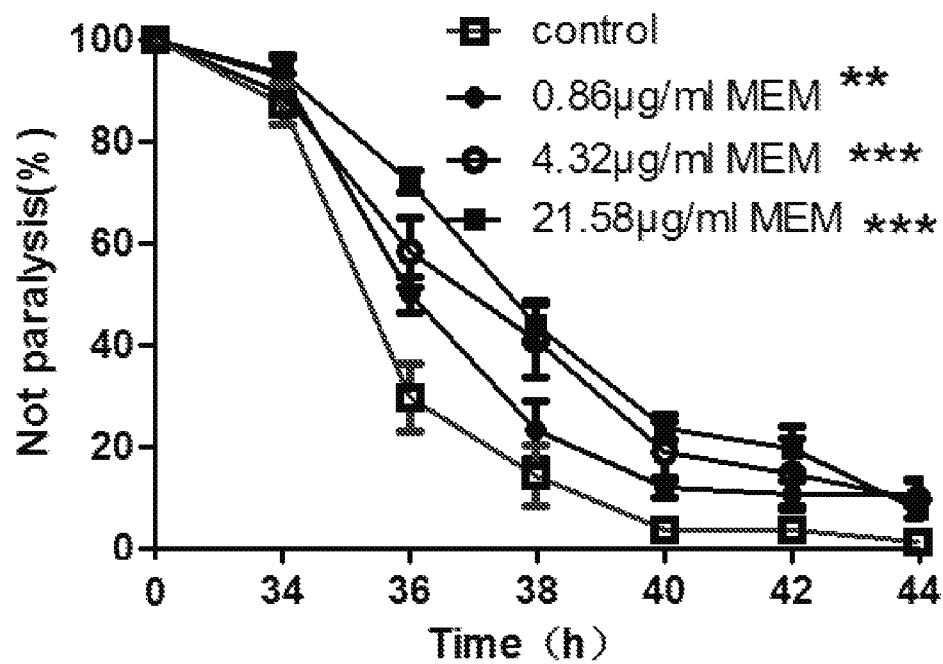
FIG. 1 illustrates the impact of positive control memantine Hydrochloride on the Aβ-induced paralysis phenotype of CL4176 strain of *C. elegans*.

The invention is further illustrated with reference to the following examples, which are not intended to limit the scope of the invention as claimed in any way, so as to achieve use of the Chinese medicine compositions and DXN of the present invention in the preparation of a medicament in the treatment or prevention of AD.

EXAMPLE 1

The Preparation of Chinese Medicine Composition Tables

1. Materials

*Valeriana* Jatamansi, Rhizoma Acori Tatarinowii, Ramulus Uncariae cum Uncis, Semen Pharbitidis, Rhizoma et Radix Nardostachys, Semen Euphorbiae, *Valeriana officinalis* and menthol crystal were purchased from Huirentang pharmacy.

Formulation 1:

This formulation consists of the following components in part by weight: *Valeriana* Jatamansi 300, Rhizoma Acori Tatarinowii 300, Semen Pharbitidis 150, Rhizoma et Radix Nardostachys 150, Ramulus Uncariae cum Uncis 150, Semen Euphorbiae 10, menthol crystal 0.1, *Valeriana officinalis* 0.45.

Formulation 2:

This formulation consists of the following components in part by weight: *Valeriana* Jatamansi 500, Rhizoma Acori Tatarinowii 500, Semen Pharbitidis 200, Rhizoma et Radix Nardostachys 200, Ramulus Uncariae cum Uncis 200, Semen Euphorbiae 15, menthol crystal 0.3, *Valeriana officinalis* 0.62.

Formulation 3:

This formulation consists of the following components in part by weight: *Valeriana* Jatamansi 600, Rhizoma Acori Tatarinowii 600, Semen Pharbitidis 300, Rhizoma et Radix Nardostachys 300, Ramulus Uncariae cum Uncis 300, Semen Euphorbiae 35, menthol crystal 0.6, *Valeriana officinalis* 0.75.

The Method of preparation of the above formulations is as follows:

The above Weigh *Valeriana* Jatamansi, Rhizoma Acori Tatarinowii, Ramulus Uncariae cum Uncis, Semen Pharbitidis, Rhizoma et Radix Nardostachys, Semen Euphorbiae, *Valeriana officinalis* and menthol crystal in proportion were taken.

*Valeriana officinalis* was pulverized into meal, and percolated the meal with 60% ethanol, then the filtrates was collected.

Three-fifths amount of total *Valeriana* Jatamansi, Rhizoma Acori Tatarinowii, and Rhizoma et Radix Nardostachys were used to extract the essential oil. The residue was mixed with Ramulus Uncariae cum Uncis, and extracted with boiling water for 1-2 times, preferably 2 times and 1-2 hours every time, preferably 1.5 hours. The filtrate was filtered and collected.

Semen Pharbitidis, and Semen Euphorbiae were pulverized into meal, and percolated the meal with 60% ethanol. Then the filtrates were collected. The filtrates were mixed and described in c part, then the mix was concentrated under vacuum and dried to obtain the extract which relative density is 1.26-1.30, preferably1.28.

Two-fifths amount of total *Valeriana* Jatamansi was crushed into fine powder. The above extract was mixed, dried and crushed into fine powder. The mix was pelletized by *Valeriana officinalis* filtrates and 70%-75% ethanol, then dried and added thereto the menthol crystal and the essential oils described above, mixed them evenly and made into tablets.

EXAMPLE 2

Effect of Memantine Hydrochloride on *C. elegans* CL4176

1. Materials (1) *C. elegans* CL4176 is purchased from Caenorhabditis Genetics Center; which is a transgenic strain and muscle-specific expression of human Aβ can be induced at 25° C., and Aβ is aggregated in muscle tissue, resulting in the paralysis of *C. elegans*. CL4176 worm was used in the invention as a pathological model to screen and evaluate the anti-AD actions of the Chinese medicine compositions and DXN.

(2) *Escherichia Coli* OP50 is purchased from Caenorhabditis Genetics Center and used as food source for *C. elegans*.

2. Reagent (1) Menantine hydrochloride (MEM), Chemical name: 1-amino-3,5-dimethyl amantadine hydrochloride, molecular formula: $C12H21N.HCl$. MEM was purchased from J&K Chemicals (CAS:41100-52-1). Memantine Hydrochloride is a noncompetitive NMDA receptor antagonist, and is used for the treatment of moderate to severe AD. It has been reported that Menantine hydrochloride (2.16 mg/mL) could significantly delay Aβ-induced paralysis in the transgenic CL4176 *C. elegans*, so Menantine hydrochloride was used as a positive control/medicament in this example.

(2) Composition and preparation of solid Nematode Growth Medium (NGM) (1 L)

| composition | Weight (g) |
|---|---|
| NaCl | 3.00 |
| $K_2HPO_4$ | 2.34 |
| $KH_2PO_4$ | 17.23 |
| Peptone | 2.50 |
| Agar | 17.00 |
| Supply $ddH_2O$ to | 1000 mL |

The solid NGM was prepared according to the above formula, and followed by autoclaved at 121° C. for 20 minutes, then added 1 mL 5 mg/mL cholesterol, 1mL 1M MgSO4, 1mL 1M CaCl2 to the sterilized NGM in a bacteria-free operating environment, then shaked well, and eventually poured into 9 cm sterilized dishes (about 20 mL/plate). The media was allowed to stand for solidification for further use.

(3) Preparation of NGM containing Menantine Hydrochloride

Stock solution of Menantine Hydrochloride (2.16mg/mL) was prepared with distilled water and directly dissolved in the NGM. The final concentration of Menantine Hydrochloride in NGM was 215.76 μg/mL, 107.88m/mL, 21.58 μg/mL, 4.32m/mL, 0.86m/mL, respectively.

In the blank control, memantine hydrochloride was replaced with the same volume of sterile water under the same preparation conditions.

*E. coli* OP50 was uniformly coated on the surface of the NGM as the food source of *C. elegans*.

(4) Formulation of M9 Solution (1L)

| composition | Weight (g) |
|---|---|
| $Na_2HPO_4$ | 6.00 |
| $KH_2PO_4$ | 3.00 |
| NaCl | 5.00 |
| 1M $MgSO_4$ | 1.00 mL |
| Supply $ddH_2O$ to | 1000 mL |

(5) Preparation of Lysis Solution 6.4% of NaClO3 solution and 1 M NaOH solution were mixed by volume ratio of 1: 1.

3. Steps of implementation (1) Culture of *C. elegans*

CL4176 worms were propagated and inoculated on solid NGM which seeded with *E. coli* (OP50) as food source and incubated in an incubator at 16° C. Worms were synchronized by lysis solution when they were grown into adults.

(2) Synchronizing Worms

An NGM medium containing large numbers of adult worms and some of the worms eggs which have been hatched was selected, and the worms were washed out from the medium with M9 solution and transferred to a centrifuge tube. The worms were allowed to settle to the bottom of the tube and the supernatant was discarded. According to the amount of warms, the basic lysate of warms was added into the centrifuge tube, and the oscillation was performed on the swirling blender for 5-7 minutes, and the vortex was stopped until all the worms were broken. The worms were packed in 1.5 mL centrifuge tube, and the worms eggs were washed with M9 solution three times.

(3) Effect of Memantine Hydrochloride on *C. elegans* CL4176

The synchronized *C. elegans* eggs were placed onto solid NGM coated with OP50 and containing different concentration of Memantine Hydrochloride. The blank control is a NMG medium coated with OP50 and added with the same volume of ddH2O to replace the Memantine Hydrochloride. The worms were cultured at 16° C. for 3 days to L3 larvae (about 60 worms per plate). The results are presented as the average of three biological replicates.

In order to induce the Aβ expression, the culture temperature of transgenic L3 larvae *C. elegans* CL4176 was shifted from 16° C. to 25° C. for 34 h. Then paralysis individuals were counted under a dissecting stereo microscope at 2 h intervals until all worms became paralyzed. The body of worms was prodded with a platinum picker, and a worm which did not show a full body wave or only moved its head was considered as paralyzed. The results were showed in FIG. 1.

As shown in the FIG. 1, positive medicament Menantine Hydrochloride significantly delayed the paralysis of the CL4176 animals in a dose-dependent manner on 21.58m/mL, 4.32 µg/mL, and 0.86m/mL, and 215.76 m/mL and 107.88 m/mL of Menantine Hydrochloride can strongly inhibit the development of *C. elegans*. The results indicated that the experimental system and model were successfully established, and the transgenic *C. elegans* CL4176 can be employed as a model in screening drugs for preventing or treating AD.

EXAMPLE 3

The Effect of the Chinese Medicine Composition on Aβ-Induced Paralysis in *C. elegans* CL4176

1. Materials are the same as described in Example 2.
2. Reagent (1) The following tables of Chinese medicine composition were the preparations prepared as described in Example 1: Formulation 1 Chinese medicine composition tables, Formulation 2 Chinese medicine composition tables, Formulation 3 Chinese medicine composition tables.

(2) Preparation of solid NGM is the same as described in Example 2 (in 1 L).

(3) Preparation of NGM containing the Chinese medicine composition.

First, the tables of Chinese medicine composition was grinded into a powder, which was dissolved in ddH2O to 150 mg/mL. Next, the solution was sonicated for 30 min at room temperature, and centrifuged at 10000 rpm for 10 min. The supernatant was collect and stored at 4° C. Stock solution of the Chinese medicine composition was made with distilled water and directly dissolved in NGM. The working concentration of the Chinese medicine composition was 1 mg/mL, 5 mg/mL, and 15 mg/mL, respectively. The working concentration of the Chinese medicine composition was replaced by the same volume of ddH2O so as to use as the blank control.

*E. coli* OP50 was coated on the surface of the NGM as the food source of *C. elegans*.

(4) Preparation of M9 is the same as described in Example 2.

(5) Preparation of lysis solution is the same as described in Example 2.

3. Steps of implementation (1) *C. elegans* culture condition is the same as described in Example 2.

(2) Synchronizing worms is the same as described in Example 2.

(3) Effect of the Chinese medicine composition on *C. elegans* CL4176

The synchronized *C. elegans* eggs were placed onto solid NGM coated with OP50 and containing working concentration of the Chinese medicine compositions. The blank control is a NMG medium coated with OP50 and added with the same volume of ddH2O to replace the Memantine Hydrochloride. The worms were cultured at 16° C. for 3 days to L3 larvae (about 60 worms per plate). The results are presented as the average of three biological replicates.

In order to induce the Aβ expression, the culture temperature of transgenic L3 larvae *C. elegans* CL4176 was shifted from 16° C. to 25° C. for 34 h. Then paralysis individuals were counted under a dissecting stereo microscope at 2 h intervals until all worms became paralyzed. The body of worms was prodded with a platinum picker, and a worm which did not show a full body wave or only moved its head was considered as paralyzed. The results were showed in FIGS. 2, 3, and 4.

Figure 2:
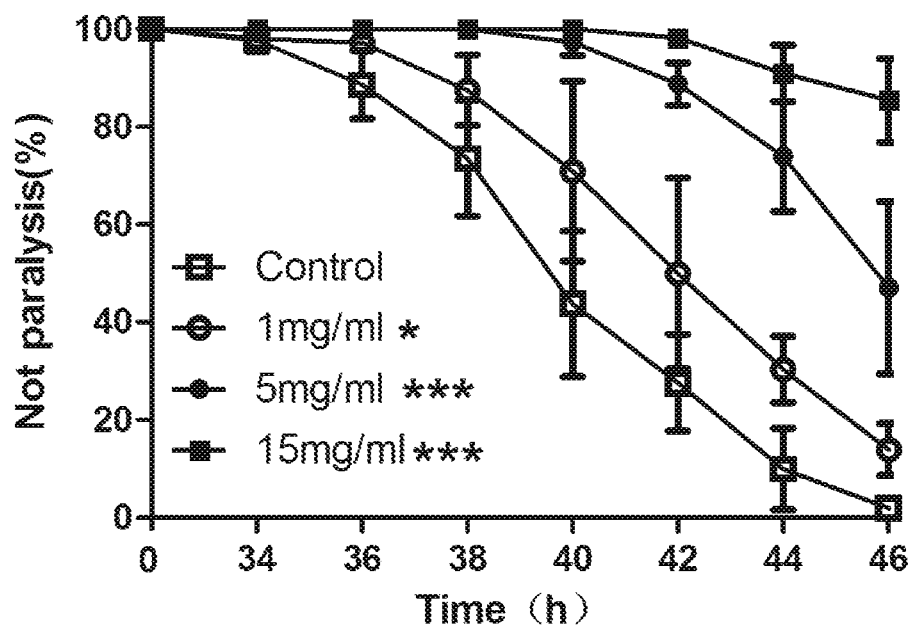
FIG. 2 illustrates the impact of formula 1 in the treatment of Alzheimer's disease in the *Caenorhabditis elegans*.
Figure 3:
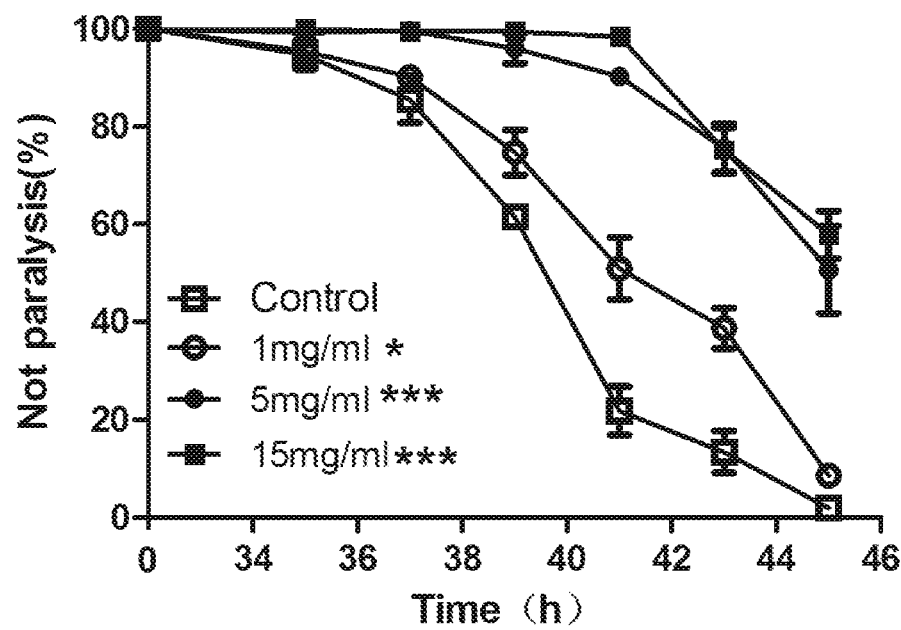
FIG. 3 illustrates the impact of formula 2 in the treatment of Alzheimer's disease in the *Caenorhabditis elegans*.
Figure 4:
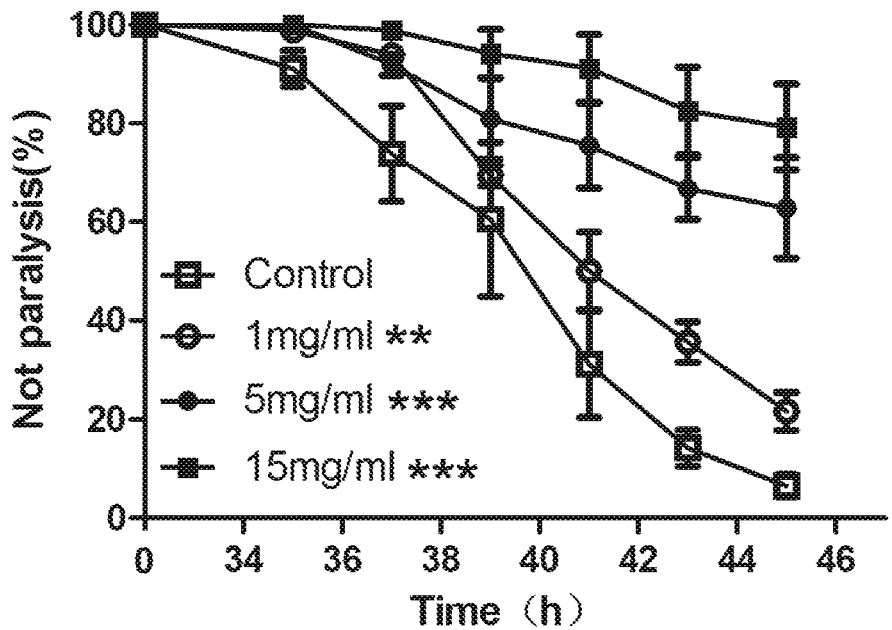
FIG. 4 illustrates the impact of formula 3 in the treatment of Alzheimer's disease in the *Caenorhabditis elegans*.

It can be seen from FIGS. 2, 3, and 4 that Formulations 1, 2, and 3 all can significantly inhibit the Aβ expression induced paralysis (P<0.001). Among them, the Formulation 2 is the best composition to inhibit the Aβ expression induced paralysis. At 44 h, the un-paralysis proportion of Formulation 2 (15 mg/mL and 5 mg/mL) still maintains at about 80% (FIG.3). However, the un-paralysis proportion of Formulations 1 and 3 were lower than 80% (FIG.s 2, and 4).

In conclusion, it can be seen from the above example that the Chinese medicine composition can significantly inhibit the Aβ expression induced paralysis, indicated that the Chinese medicine composition has potential as a drug for preventing or treating AD. Therefore, the Chinese medicine composition disclosed in present invention can be applied in the preparation of drugs which preventing or treating AD.

EXAMPLE 4

Effect of DXN on *C. elegans* CL4176

1. Materials is the same as described in Example 2.
2. Reagent (1) Dianxianning tablet (DXN) was produced by Kunming factory of traditional Chinese medicament, and the approved number is Z53020771.

(2) Preparation of solid NGM is the same as described in Example 2 (in 1 L), which is the same as Example 2.

(3) Preparation of NGM medium containing DXN

First, DXN was heated by the flame to remove the sugar-coating. Then, the sugar-coating free DXN was grinded into a powder; the powder was dissolved in ddH2O to formulate 150 mg/mL of the aqueous solution of DXN tablet. Next, the solution was sonicated for 30 min at room temperature, and centrifuged at 10000 rpm for 10 min. The supernatant was taken and stored at 4° C. Stock solution of DXN was made with distilled water and directly dissolved in NGM. The working concentration of DXN was 1 mg/mL, 5 mg/mL, 15 mg/mL, respectively. The working concentration of DXN was replaced by the same volume of ddH2O as the blank control.

*E. coli* OP50 was coated on the surface of the NGM as the food source of *C. elegans*.

(4) Preparation of M9 is the same as described in Example 2.

(5) Preparation of lysis solution is the same as described in Example 2.

3. Steps of implementation (1) *C. elegans* culture condition is the same as described in Example 2.

(2) Synchronizing worms is the same as described in Example 2.

(3) Effect of DXN on *C. elegans*. CL4176

The synchronized *C. elegans* eggs were placed onto solid NGM coated with OP50 and containing working concentration of DXN. The blank control is a NMG medium coated with OP50 and added with the same volume of ddH2O to replace the Memantine Hydrochloride. The worms were cultured at 16° C. for 3 days to L3 larvae (about 60 worms per plate). The results are presented as the average of three biological replicates.

In order to induce the Aβ expression, the culture temperature of transgenic L3 larvae *C. elegans* CL4176 was shifted from 16° C. to 25° C. for 34 h. Then paralysis individuals were counted under a dissecting stereo microscope at 2 h intervals until all worms became paralyzed. The body of worms was prodded with a platinum picker, and a worm which did not show a full body wave or only moved its head was considered as paralyzed. The results showed in FIG. 5.

Figure 5:
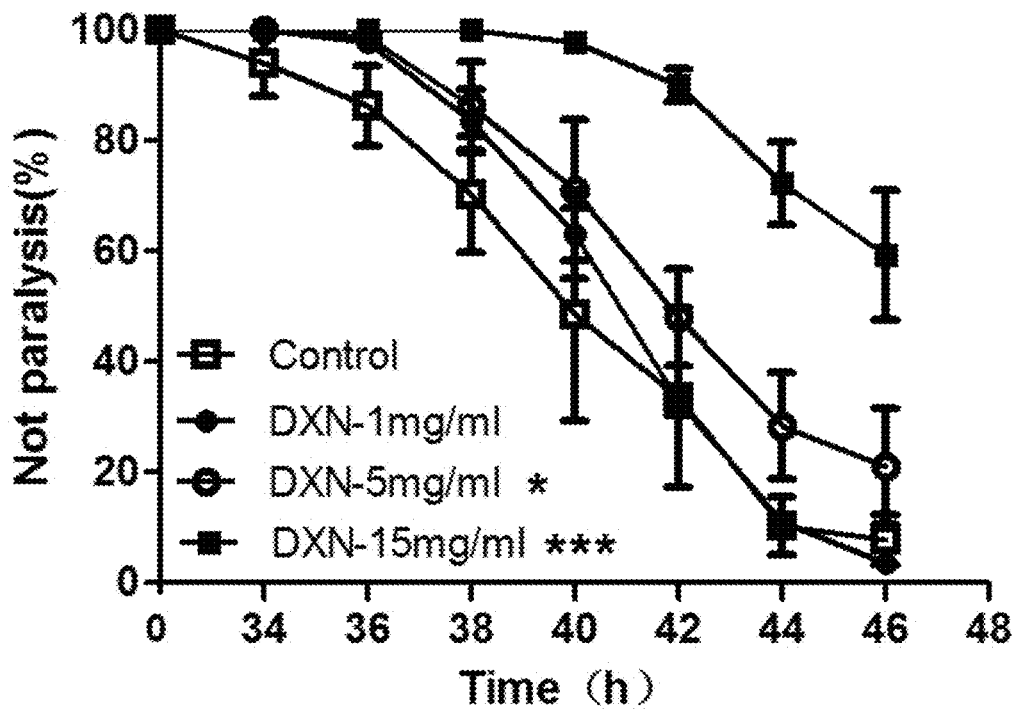
FIG. 5 illustrates the impact of DXN on the Aβ-induced paralysis phenotype of CL4176 strain of *C. elegans*.

It can be seen from FIG. 5 that DXN can significantly inhibit the Aβ expression induced paralysis at 15 mg/mL and 5 mg/mL, and especially the 15 mg/mL DXN can dramatically inhibit the Aβ expression induced paralysis (P<0.001), and the groups have the dose-effect relationship.

The present invention shows that DXN can significantly ameliorate Aβ-induced paralysis in the transgenic *C. elegans* expressing Aβ, which indicated that DXN has potential as a drug for preventing or treating AD. Meanwhile, novel application of DXN disclosed in the present invention will expand the indications of DXN which may be useful in preventing or treating AD.

EXAMPLE 5

Comparison of Effect and Toxicity Between the Chinese Medicine Compositions

1. Materials is the same as described in Example 2.
2. Reagent (1) The tables of the Chinese medicine composition were the preparations prepared as described in Example 1. Specifically, the used Chinese medicine composition is the Formulation 2 Chinese medicine composition tables.

(2) *Valeriana* Jatamansi, Rhizoma Acori Tatarinowii, Ramulus Uncariae cum were purchased from Huirentang pharmacy.

(3) Preparation of NGM is the same as described in Example 2.

(4) Preparation of NGM containing the Chinese medicine composition.

First, the tables of the Chinese medicine composition were grinded into a powder, which was dissolved in ddH2O to 150 mg/mL. Next, the solution was sonicated for 30 min at room temperature, and centrifuged at 10000 rpm for 10 min. The supernatant was collected and stored at 4° C. Stock solution of the Chinese medicine composition was made with distilled water and directly dissolved in NGM. The working concentration of the Chinese medicine composition was 1 mg/mL, 5 mg/mL, and 15 mg/mL, respectively.

(5) Preparation of *Valeriana* Jatamansi extract and NGM containing *Valeriana* Jatamansi extract Three-fifths amount of total *Valeriana* Jatamansi was used to extract essential oil, and the residue was extracted with boiling water for 1-2 times, preferably 2 times and 1-2 hours every time, preferably 1.5 hours, filtered it and collected the filtrate. The filtrate was concentrated under vacuum and reduced pressure and dried to obtain the extract which has relative density of 1.26-1.30, preferably1.28. Two-fifths amount of total *Valeriana* Jatamansi was grinded into fine powder. The essential oil, the extracts and the powder of *Valeriana* Jatamansi were uniformly mixed, and dissolved in distilled water to formulate the aqueous solution of *Valeriana* Jatamansi. The mixture was sonicated for 30 min at room temperature, and centrifuged at 10000 rpm for 10 min. The supernatant was collected and stored at 4° C. Stock solution of *Valeriana* Jatamansi extract was directly dissolved in NGM and the working concentration of *Valeriana* Jatamansi is the same as NGM containing Formulation 2.

(6) Preparation of Rhizoma Acori Tatarinowii extract and NGM containing Rhizoma Acori Tatarinowii extract Rhizoma Acori Tatarinowii was used to extract essential oil, after that the residue was extracted with boiling water for 1-2 times, preferably 2 times and 1-2 hours every time, preferably 1.5 hours. It was filtered and the filtrate is combined. The filtrate was concentrated under vacuum and reduced pressure and dried to obtain the extract which has relative density of 1.26-1.30, preferably 1.28. The essential oil and the extracts of *Valeriana* Jatamansi were mixed, and dissolved in distilled water to formulate the solution of Rhizoma Acori Tatarinowii. The mixture was sonicated for 30 min at room temperature, and centrifuged at 10000 rpm for 10 min. The supernatant was collected and stored at 4° C. Stock solution of Rhizoma Acori Tatarinowii extract was directly dissolved in NGM and the working concentration of Rhizoma Acori Tatarinowii is the same as NGM containing Formula 2.

(7) Preparation of Ramulus Uncariae cum Uncis Extract and NGM Containing Ramulus Uncariae cum Uncis Extract Ramulus Uncariae cum Uncis was extracted with boiling water for 1-2 times, preferably 2 times and 1-2 hours every time, preferably 1.5 hours. It was filtered and collected the filtrate, and then the filtrate was concentrated under vacuum and reduced pressure and dried to obtain the extract which has relative density of 1.26-1.30, preferably1.28. Extract of Ramulus Uncariae cum Uncis was dissolved in distilled water. The mixture was sonicated for 30 min at room temperature, and centrifuged at 10000 rpm for 10 min. The supernatant was collected and stored at 4° C. Stock solution of Ramulus Uncariae cum Uncis extract was directly dissolved in NGM and the working concentration of Ramulus Uncariae cum Uncis is the same as NGM containing Formula 2.

(8) Preparation of *Valeriana* Jatamansi, Ramulus Uncariae cum Uncis and Rhizoma Acori Tatarinowii extract and NGM containing above extract Rhizoma Acori Tatarinowii and three-fifths amount of total *Valeriana* Jatamansi were used to extract essential oil. The residue was mixed with Ramulus Uncariae cum Uncis, and extracted with boiling water for 1-2 times, preferably 2 times and 1-2 hours every time, preferably 1.5 hours. It was filtered and collected the filtrate, then the filtrate was concentrated under vacuum and reduced pressure and dried to obtain the extract which has relative density of 1.26-1.30, preferably1.28. Two-fifths amount of total *Valeriana* Jatamansi was crushed into fine powder. The above essential oils, the extracts and the powder of *Valeriana* Jatamansi were mixed, and dissolved in distilled water. The mixture was sonicated for 30 min at room temperature, and centrifuged at 10000 rpm for 10 min. The supernatant was collected and stored at 4° C. Stock solution of extract was directly dissolved in NGM and the working concentration of *Valeriana* Jatamansi, Ramulus Uncariae cum Uncis and Rhizoma Acori Tatarinowii are the same as NGM containing Formulation 2.

The working concentration of Formula 2 was replaced by the same volume of ddH2O as the blank control.

*E. coli* OP50 was coated on the surface of the NGM as the food source of *C. elegans*.

(9) Preparation of M9 is the same as described in Example 2.

(10) Preparation of lysis solution is the same as described in Example 2.

3. Steps of implementation (1) *C. elegans* culture condition is the same as described in Example 2.

(2) Synchronizing worms is the same as described in Example 2.

(3) The Comparison between the Chinese medicine compositions and its single herb on ameliorating Aβ expression-induced paralysis in CL4176 worms The synchronized *C. elegans* eggs were placed onto solid NGM with OP50 seeded and containing the Chinese medicine compositions or the extracts of *Valeriana* Jatamansi, Acorus gramineus, Uncaria tomentosa. The blank control is a NMG medium coated with OP50 and added with the same volume of ddH2O to replace the Chinese medicine compositions. The worms were cultured at 16° C. for 3 days to L3 larvae (about 60 worms per plate) and the results are presented as the average of three biological replicates.

In order to induce the Aβ expression, the culture temperature of transgenic L3 larvae *C. elegans* CL4176 was shifted from 16° C. to 25° C. for 34 h. Then paralysis individuals were counted under a dissecting stereo microscope at 2 h intervals until all worms became paralyzed. The body of worms was prodded with a platinum picker, and a worm which did not show a full body wave or only moved its head was considered as paralyzed. The results were showed in FIG. 6.

Figure 6:
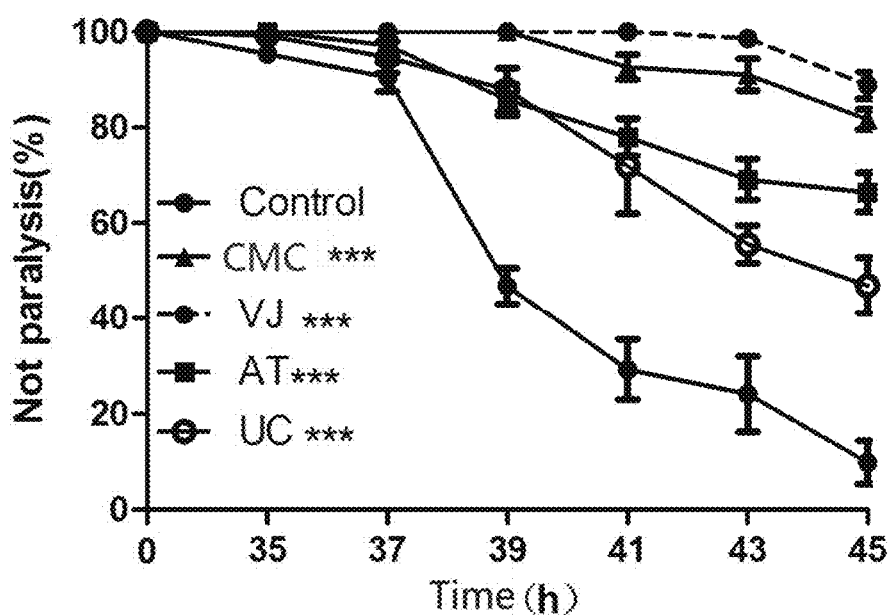
FIG. 6 illustrates the impact of *Valeriana* Jatamansi (VJ), Ramulus Uncariae cum Uncis (UC), Rhizoma Acori Tatarinowii (AT) and the Chinese medicine composition (CMC) in the treatment of Alzheimer's disease in the *Caenorhabditis elegans*.

From Figure.6, the results showed that *Valeriana* Jatamansi (VJ), Rhizoma Acori Tatarinowii (AT), Ramulus Uncariae cum Uncis (UC) and the Chinese medicine compositions (CMC) all can significantly delay the paralysis of the CL4176 animals (p<0.001). Among them, *Valeriana* Jatamansi had the best inhibition effect on the Aβ-induced paralysis in worms, and the effect is almost equal to Chinese medicine compositions. The effect of Rhizoma Acori Tatarinowii and Ramulus Uncariae cum Uncis are lower than the Chinese medicine compositions (P<0.001). *Valeriana* Jatamansi combined with Rhizoma Acori Tatarinowii and Ramulus Uncariae cum Uncis seriously affect the growth and development of worms, the eggs of *C. elegans* even could not be hatched. The results indicated that the toxicity of the three herbs was increased after combined each other.

(4) The toxicity comparison of the Chinese medicine compositions and its single herbs.

Figure 8:
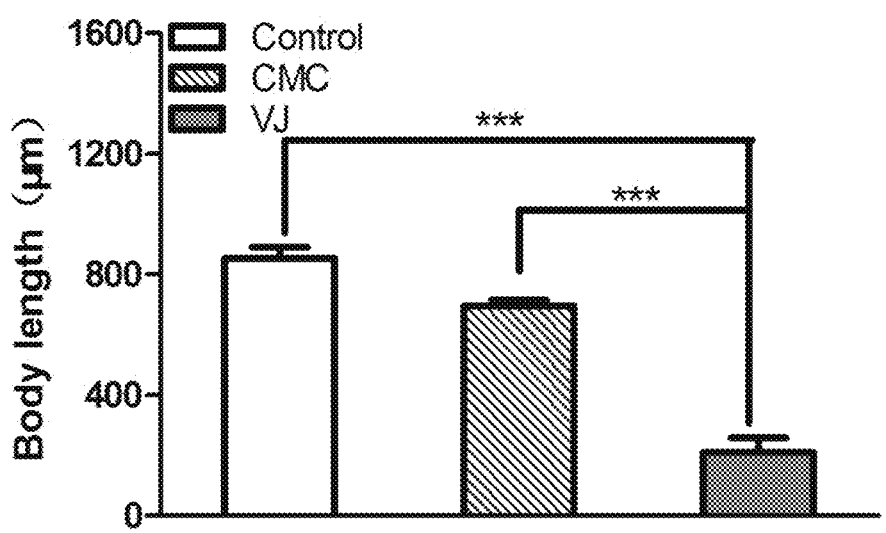
FIG. 8 illustrates the toxicity of *Valeriana* Jatamansi (VJ) and the Chinese medicine composition (CMC) in the *Caenorhabditis elegans*.

After the end of paralysis experiment, worms were immediately placed at 50° C. for 15 min to straighten the body of every worm. The worms were observed and photographed under a microscope, and measured the length of every worm using MvImage system. The results were shown in FIG. 8.

The results showed that *Valeriana* Jatamansi can significantly decrease the length of worms compared with the control group and the Chinese medicine compostion group, indicated that *Valeriana* Jatamansi significantly suppressed the growth and development of *C. elegans* and the toxicity is higher than the Chinese medicine composition.

*Valeriana* Jatamansii, Ramulus Uncariae cum Uncis, Rhizoma Acori Tatarinowii and the Chinese medicine composition all can significantly suppress the Aβ expression induced paralysis. Among them, *Valeriana* Jatamansii and the Chinese medicine composition have a better suppression effect on Aβ expression induced paralysis. The results of the toxicity comparison of the Chinese medicine composition and its single herbs showed that Valeriana Jatamansi significantly suppressed the growth and development of *C. elegans*, but the Chinese medicine composition almost had no effect on the growth and development of *C. elegans*. The results indicated that the toxicity of the Chinese medicine composition is significantly lower than *Valeriana* Jatamansi.

In conclusion, these results showed that the Chinese medicine composition has significantly effect on suppressing the Aβ-induced paralysis in the transgenic *C. elegans* expressing Aβ and has lower toxicity on the development of *C. elegans*. The results indicated that the Chinese medicine composition is likely to be a potential drug candidate to protect against ADs because of its low toxicity and high treatment effect. In conclusion, the Chinese medicine composition has the potential to prevent or treat AD, and it can be used in the preparation of a medicine in the treatment or prevention of AD.

EXAMPLE 6

Comparison of Effect and Toxicity Between DXN and its Single Herb

1. Materials is the same as described in Example 2.
2. Reagent (1) Dianxianning tablet (DXN) was produced by Kunming factory of traditional Chinese medicament, and the approval number is Z53020771.

(2) *Valeriana* Jatamansi, Rhizoma Acori Tatarinowii, Ramulus Uncariae cum Uncis were purchased from Huirentang pharmacy.

(3) Preparation of NGM is the same as described in Example 2.

(4) Preparation of NGM containing DXN.

First, DXN was heated by the flame to remove the sugar-coating. Then, the sugar-coating free DXN was grinded into a powder; the powder was dissolved in ddH2O to formulate 150 mg/mL of the aqueous solution of DXN tablet. Next, the solution was sonicated for 30 min at room temperature, and centrifuged at 10000 rpm for 10 min. The supernatant was taken and stored at 4° C. Stock solution of DXN was made with distilled water and directly dissolved in NGM to formulate a NGM medium containing 15 mg/mL of the working concentration of DXN.

(5) Preparation of *Valeriana* Jatamansi extract and NGM containing *Valeriana* Jatamansi extract Three-fifths amount of total *Valeriana* Jatamansi was used to extract essential oil, and the residue was extracted with boiling water for 1-2 times, preferably 2 times and 1-2 hours every time, preferably 1.5 hours. The mixture was filtered and the filtrate was collected. The filtrate was concentrated under vacuum and reduced pressure and dried to obtain the extract which has relative density of 1.26-1.30, preferably 1.28. Two-fifths amount of total *Valeriana* Jatamansi was grinded into fine powder. The essential oil, the extracts and the powder of *Valeriana* Jatamansi were uniformly mixed, and dissolved in distilled water to formulate the aqueous solution of *Valeriana* Jatamansi. The mixture was sonicated for 30 min at room temperature, and centrifuged the mixture at 10000 rpm for 10 min. The supernatant was collected and stored at 4° C. Stock solution of *Valeriana* Jatamansi extract was directly dissolved in NGM and the working concentration of *Valeriana* Jatamansi is the same as NGM containing DXN.

(6) Preparation of Rhizoma Acori Tatarinowii extract and NGM containing Rhizoma Acori Tatarinowii extract Rhizoma Acori Tatarinowii was used to extract essential oil, after that the residue was extracted with boiling water for 1-2 times, preferably 2 times and 1-2 hours every time, preferably 1.5 hours. The mixture was filtered and the filtrate was collected. The filtrate was concentrated under vacuum and reduced pressure and dried to obtain the extract which has relative density of 1.26-1.30, preferably 1.28. The essential oil and the extracts of *Valeriana* Jatamansi were mixed, and dissolved in distilled water to formulate the solution of Rhizoma Acori Tatarinowii. The mixture was sonicated for 30 min at room temperature, and centrifuged at 10000 rpm for 10 min. The supernatant was collected and stored at 4° C. Stock solution of Rhizoma Acori Tatarinowii extract was directly dissolved in NGM and the working concentration of Rhizoma Acori Tatarinowii is the same as NGM containing DXN.

(7) Preparation of Ramulus Uncariae cum Uncis extract and NGM containing Ramulus Uncariae cum Uncis extract Ramulus Uncariae cum Uncis was extracted with boiling water for 1-2 times, preferably 2 times and 1-2 hours every time, preferably 1.5 hours. The mixture was filtered and the filtrate was collected. Then the filtrate was concentrated under vacuum and reduced pressure and dried to obtain the extract which has relative density of 1.26-1.30, preferably 1.28. Extract of Ramulus Uncariae cum Uncis was dissolved in distilled water. The mixture was sonicated for 30 min at room temperature, and centrifuged at 10000 rpm for 10 min. The supernatant was collected and stored at 4° C. Stock solution of Ramulus Uncariae cum Uncis extract was directly dissolved in NGM and the working concentration of Ramulus Uncariae cum Uncis is the same as NGM containing DXN (8) Preparation of *Valeriana* Jatamansi, Ramulus Uncariae cum Uncis and Rhizoma Acori Tatarinowii extract and NGM containing above extract Rhizoma Acori Tatarinowii and three-fifths amount of total *Valeriana* Jatamansi were used to extract essential oil, and the residue was mixed with Ramulus Uncariae cum Uncis, extracted with boiling water for 1-2 times, preferably 2 times and 1-2 hours every time, preferably 1.5 hours. The mixture was filtered and the filtrate was collected. The filtrate then was concentrated under vacuum and reduced pressure and dried to obtain the extract which has relative density of 1.26-1.30, preferably 1.28. Two-fifths amount of total *Valeriana* Jatamansi was crushed into fine powder. The above essential oils, the extracts and the powder of Valeriana Jatamansi were mixed, and dissolved in distilled water. The mixture was sonicated for 30 min at room temperature, and centrifuged at 10000 rpm for 10 min. The supernatant was collected and stored at 4° C. Stock solution of extract was directly dissolved in NGM and the working concentration of *Valeriana* Jatamansi, Ramulus Uncariae cum Uncis and Rhizoma Acori Tatarinowii are the same as NGM containing DXN.

The working concentration of DXN was replaced by the same volume of ddH2O as the blank control.

*E. coli* OP50 was coated on the surface of the NGM as the food source of *C. elegans*.

(9) Preparation of M9 is the same as described in Example 2.

(10) Preparation of lysis solution is the same as described in Example 2.

3. Steps of implementation (1) *C. elegans* culture condition is the same as described in Example 2.

(2) Synchronizing worms is the same as described in Example 2.

(3) The Comparison between DXN and its single herb on ameliorating Aβ expression-induced paralysis in CL4176 worms The synchronized *C. elegans* eggs were placed onto solid NGM with OP50 seeded and containing DXN or the extracts of *Valeriana* Jatamansi, Acorns gramineus, Uncaria tomentosa. The blank control is a NMG medium coated with OP50 and added with the same volume of ddH2O to replace DXN. The worms were cultured at 16° C. for 3 days to L3 larvae (about 60 worms per plate) and the results are presented as the average of three biological replicates.

In order to induce the Aβ expression, the culture temperature of transgenic L3 larvae *C. elegans* CL4176 was shifted from 16° C. to 25° C. for 34 h. Then paralysis individuals were counted under a dissecting stereo microscope at 2 h intervals until all worms became paralyzed. The body of worms was prodded with a platinum picker, and a worm which did not show a full body wave or only moved its head was considered as paralyzed. The results were showed in FIG. 7.

Figure 7:
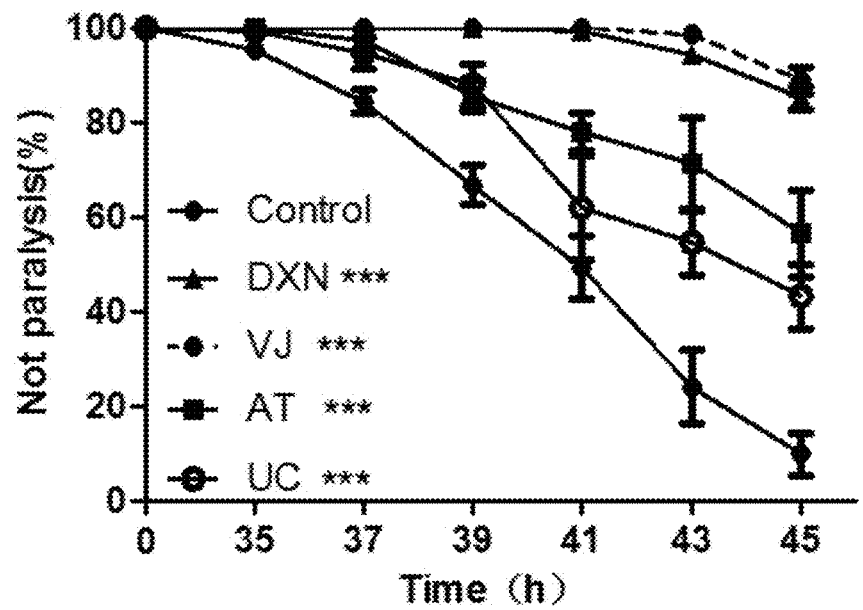
FIG. 7 illustrates the efficacy assessment results of *Valeriana* Jatamansi (VJ), Ramulus Uncariae cum Uncis (UC), Rhizoma Acori Tatarinowii (AT) and DXN tablet on the treatment of AD.

It can be seen from the result of FIG. 7 that *Valeriana* Jatamansi, Rhizoma Acori Tatarinowii and Ramulus Uncariae cum Uncis all can significantly delay the paralysis of the CL4176 animals (p<0.001), especially *Valeriana* Jatamansi can dramatically ameliorate Aβ-induced paralysis in worms, which is roughly the same as DXN but far better than Rhizoma Acori Tatarinowii and Ramulus Uncariae cum Uncis (P<0.001).

(4) The toxicity comparison of DXN and its single herbs.

Figure 9:
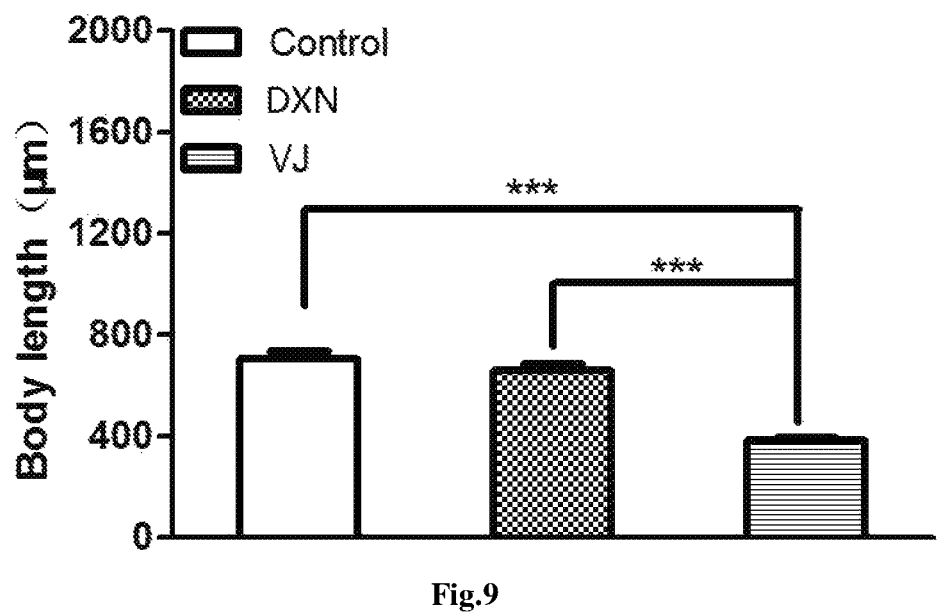
FIG. 9 illustrates the toxicity assessment results of *Valeriana* Jatamansi (VJ) and DXN tablet in the *C. elegans*.

After the end of paralysis experiment, worms were immediately placed at 50° C. for 15 min to straighten the body of every worm. The worms were observed and photographed under a microscope, and measured the length of every worm using MvImage system. The results were shown in FIG. 9.

The results showed that *Valeriana* Jatamansi (VJ) can significantly decrease the length of worms compared with the control group and DXN group, indicated that *Valeriana* Jatamansi significantly suppressed the growth and development of *C. elegans* and the toxicity is higher than DXN.

*Valeriana* Jatamansii, Ramulus Uncariae cum Uncis, Rhizoma Acori Tatarinowii and DXN all can significantly suppress the Aβ expression induced paralysis. Among them, Valeriana Jatamansii and the DXN have a better suppression effect on Aβ expression induced paralysis. The results of the toxicity comparison of DXN and its single herbs showed that *Valeriana* Jatamansi significantly suppressed the growth and development of *C. elegans*, but DXN almost had no effect on the growth and development of *C. elegans*. The results indicated that the toxicity of DXN is significantly lower than *Valeriana* Jatamansi.

In conclusion, these results showed that DXN has significant effect on suppressing the Aβ-induced paralysis in the transgenic *C. elegans* expressing Aβ and has lower toxicity on the development of *C. elegans*. The results indicated that DXN was likely to be a potential drug candidate to protect against AD because of its low toxicity and high treatment effect. The novel application of the present invention expanded the indications of DXN that DXN can be used in the preparation of a medicament in the treatment or prevention of AD.

We claim:

1. A method for inhibiting β-amyloid protein expression, comprising administering a Chinese medicine composition comprising *Valeriana* Jatamansi, Rhizoma Acori Tatarinowii, Ramulus Uncariae cum Uncis, Semen Pharbitidis, Rhizoma et Radix Nardostachys, Semen Euphorbiae, *Valeriana officinalis* and menthol crystal.

2. The method of claim 1, wherein the Chinese medicine composition comprises the following components in part by weight: 300 to 600 parts of *Valeriana Jatamansi*, 300 to 600 parts of Rhizoma Acori Tatarinowii, 150 to 300 parts of Ramulus Uncariae cum Uncis, 150 to 300 parts of Semen Pharbitidis, 150 to 300 parts of Rhizoma et Radix Nardostachys 10 to 35 parts of Semen Euphorbiae, 0.45 to 0.75 parts of *Valeriana* officinalis and 0.1 to 0.6 parts of menthol crystal.

3. The method of claim 2, wherein the Chinese medicine composition comprises the following components in part by weight: 300 to 500 parts of *Valeriana* Jatamansi, 300 to 500 parts of Rhizoma Acori Tatarinowii, 150 to 200 parts of Ramulus Uncariae cum Uncis, 150 to 200 parts of Semen Pharbitidis, 150 to 200 parts of Rhizoma et Radix Nardostachys 10 to 15 parts of Semen Euphorbiae, 0.45 to 0.62 parts of *Valeriana officinalis* and 0.1 to 0.3 parts of menthol crystal.

4. The method of claim 2, wherein the Chinese medicine composition comprises the following components in part by weight: 500 to 600 parts of *Valeriana* Jatamansi, 500 to 600 parts of Rhizoma Acori Tatarinowii, 200 to 300 parts of Ramulus Uncariae cum Uncis, 200 to 300 parts of Semen Pharbitidis, 200 to 300 parts of Rhizoma et Radix Nardostachys 15 to 35 parts of Semen Euphorbiae, 0.62 to 0.75 parts of *Valeriana* officinalis and 0.3 to 0.6 parts of menthol crystal.

5. A method for inhibiting β-amyloid protein expression, comprising administering Dianxianning, wherein Dianxianning comprises the following components in part by weight: 500 parts of *Valeriana* Jatamansi, 500 parts of Rhizoma Acori Tatarinowii, 200 parts of Ramulus Uncariae cum Uncis, 200 parts of Semen Pharbitidis, 200 parts of Rhizoma et Radix Nardostachys, 15 parts of Semen Euphorbiae, 0.62 parts of *Valeriana* officinalis and 0.3 parts of menthol crystal.

6. The method of claim 5, wherein the Dianxianning is in a form of tablet, pill, capsule, oral solution or granule.

7. The method of claim 6, wherein the Dianxianning is in a form of tablet.

* * * * *